US012234440B2

(12) United States Patent
Eiguren Fernandez et al.

(10) Patent No.: US 12,234,440 B2
(45) Date of Patent: Feb. 25, 2025

(54) EFFICIENT DEPOSITION OF NANO-SIZED PARTICLES ONTO CELLS AT AN AIR LIQUID INTERFACE

(71) Applicants: Aerosol Dynamics Inc., Berkeley, CA (US); University of Florida Research Foundation, Incorporated, Gainesville, FL (US)

(72) Inventors: Arantzazu Eiguren Fernandez, Richmond, CA (US); Gregory Stephen Lewis, Berkeley, CA (US); Steven Russel Spielman, Oakland, CA (US); Chang-Yu Wu, Gainesville, FL (US); Trevor Benson Tilly, Columbus, OH (US)

(73) Assignees: Aerosol Dynamics Inc., Berkeley, CA (US); University of Florida Research Foundation, Incorporated, Gainesville, FL (US)

( * ) Notice: Subject to any disclaimer, the term of this patent is extended or adjusted under 35 U.S.C. 154(b) by 435 days.

(21) Appl. No.: 16/912,486

(22) Filed: Jun. 25, 2020

(65) Prior Publication Data

US 2020/0407675 A1 Dec. 31, 2020

Related U.S. Application Data

(60) Provisional application No. 62/866,216, filed on Jun. 25, 2019.

(51) Int. Cl.
*C12M 3/00* (2006.01)
*C12M 1/00* (2006.01)
(Continued)

(52) U.S. Cl.
CPC ............ *C12M 29/08* (2013.01); *C12M 23/06* (2013.01); *C12M 23/50* (2013.01); *C12M 41/12* (2013.01);
(Continued)

(58) Field of Classification Search
CPC ........................... C12M 23/50; C12N 2513/00
See application file for complete search history.

(56) References Cited

U.S. PATENT DOCUMENTS 6,712,881 B2 3/2004 Hering et al.
8,801,838 B2 8/2014 Hering et al.
(Continued)

FOREIGN PATENT DOCUMENTS

DE 10014057 B4 * 6/2006
EP 3327439 A1 * 5/2018
(Continued)

OTHER PUBLICATIONS

English translation of JP-2010142196 to Oda, generated 2022.*
(Continued)

*Primary Examiner* — Nathan A Bowers
(74) *Attorney, Agent, or Firm* — Pearl Cohen Zedek Latzer Baratz LLP

(57) ABSTRACT

An apparatus and method for the delivery and deposition of particles air-liquid-interface (ALI) cell cultures includes a sample inlet coupled to a growth tube having interior walls that are wet. The growth tube is configured to operate at a first temperature along a first length of the tube and a second temperature along a second length positioned between the first length and a growth tube outlet. The apparatus also includes a nozzle plate having a plurality of nozzles. The exposure chamber adapted to hold cell cultures at an air-liquid interface positioned underneath the plurality of nozzles and a temperature regulator adapted to control a
(Continued)

temperature of the exposure chamber. The apparatus also includes a controller including instructions operable to cause the controller to maintain a relative humidity within the exposure chamber by controlling at least the second temperature of the growth tube and the temperature of the exposure chamber.

11 Claims, 10 Drawing Sheets

(51) Int. Cl.

| | |
|---|---|
| ***C12M 1/12*** | (2006.01) |
| ***C12M 1/34*** | (2006.01) |
| ***C12N 5/00*** | (2006.01) |

(52) U.S. Cl.

CPC ........... *C12M 41/26* (2013.01); *C12N 5/0006* (2013.01); *C12N 5/0062* (2013.01); *C12N 2500/60* (2013.01); *C12N 2513/00* (2013.01)

(56) References Cited

U.S. PATENT DOCUMENTS

| | | | | |
|---|---|---|---|---|
| 9,588,105 | B1* | 3/2017 | Hussain | C12M 29/26 |
| 2004/0020362 | A1* | 2/2004 | Hering | G01N 15/065 95/228 |
| 2005/0170499 | A1* | 8/2005 | Mohr | C12M 29/00 435/288.3 |
| 2014/0060155 | A1* | 3/2014 | Hering | G01N 1/2202 73/863.22 |

FOREIGN PATENT DOCUMENTS

| | | | |
|---|---|---|---|
| JP | 2010142196 A | * | 7/2010 |
| WO | WO-2021/104787 A1 | * | 6/2021 |

OTHER PUBLICATIONS

Eiguren-Fernandez, A. et al., "Design and Laboratory Evaluation of a Sequential Spot Sampler for Time-Resolved Measurement of Airborne Particle Composition", Aerosol Science and Technology, 2014, 48:6, pp. 655-663.

Eiguren-Fernandez, A. et al., "Time-resolved Characterization of Particle Associated Polycyclic Aromatic Hydrocarbons using a newly-developed Sequential Spot Sampler with Automated Extraction and Analysis", Atmospheric Environment, 2014, 96, pp. 125-134.

Hecobian, A. et al., "Evaluation of the Sequential Spot Sampler (S3) for time-resolved measurement of PM2.5 sulfate and nitrate through lab and field measurements", Atmos. Meas. Tech., 2016, 9, pp. 525-533.

Tilly, Trevor B. et al., "Condensational particle growth device for reliable cell exposure at the air-liquid interface to nanoparticles", Aerosol Science and Technology, 2019, 53:12, pp. 1415-1428.

Eiguren-Fernandez, A. et al., "An online monitor of the oxidative capacity of aerosols (o-MOCA)", Atmos. Meas. Tech., 2017, 10, pp. 633-644.

Pan, M. et al., "Efficient collection of viable virus aerosol through laminar-flow, water-based condensational particle growth", Journal of Applied Microbiology, 2016, 120(3), pp. 805-815.

* cited by examiner

EFFICIENT DEPOSITION OF NANO-SIZED PARTICLES ONTO CELLS AT AN AIR LIQUID INTERFACE

CLAIM OF PRIORITY

This application claims the benefit of U.S. Provisional Patent Application No. 62/866,216 filed on Jun. 25, 2019.

GOVERNMENT LICENSE RIGHTS

This invention was made with government support under National Institutes of Health contracts R21A1123933 and R43ES030649. The government has certain rights in the invention.

BACKGROUND

Exposure to airborne nanoparticles, either emitted by human processes or manufactured for industrial purposes, has been associated with many adverse health effects. The use of in vitro models continues to be the primary approach employed to identify the toxicological responses of potentially hazardous nanomaterials. These cellular models allow for detailed identification of the mechanistic processes and cellular functions affected, altered or damaged by the particles. Although in vitro models can provide fast characterization of the toxicological effects of particles, they do not mimic the human body and it's very difficult to measure the exact dose that reaches the cells.

In recent years, a new in vitro cell model that uses cells cultured at an air-liquid interface (ALI) has been employed. The ALI model more closely mimics the interface within the lung where cells are exposed to particles. Yet, for an ALI model to be representative, the method used to deliver particles to the ALI cell culture must also mimic how airborne nanomaterials are delivered to and deposited in the lung. Although considerable advances have been made, current experimental approaches and commercially available instruments used for the delivery of airborne particles to ALI cell cultures still exhibit limitations: the deposition efficiency varies with particle size and the delivery dose is not well controlled.

BRIEF DESCRIPTION OF THE DRAWINGS

Embodiments of the present technology relating to both structure and method of operation may best be understood by referring to the following description and accompanying drawings, in which similar reference characters denote similar elements throughout the several views.

SUMMARY

Figure 1A:
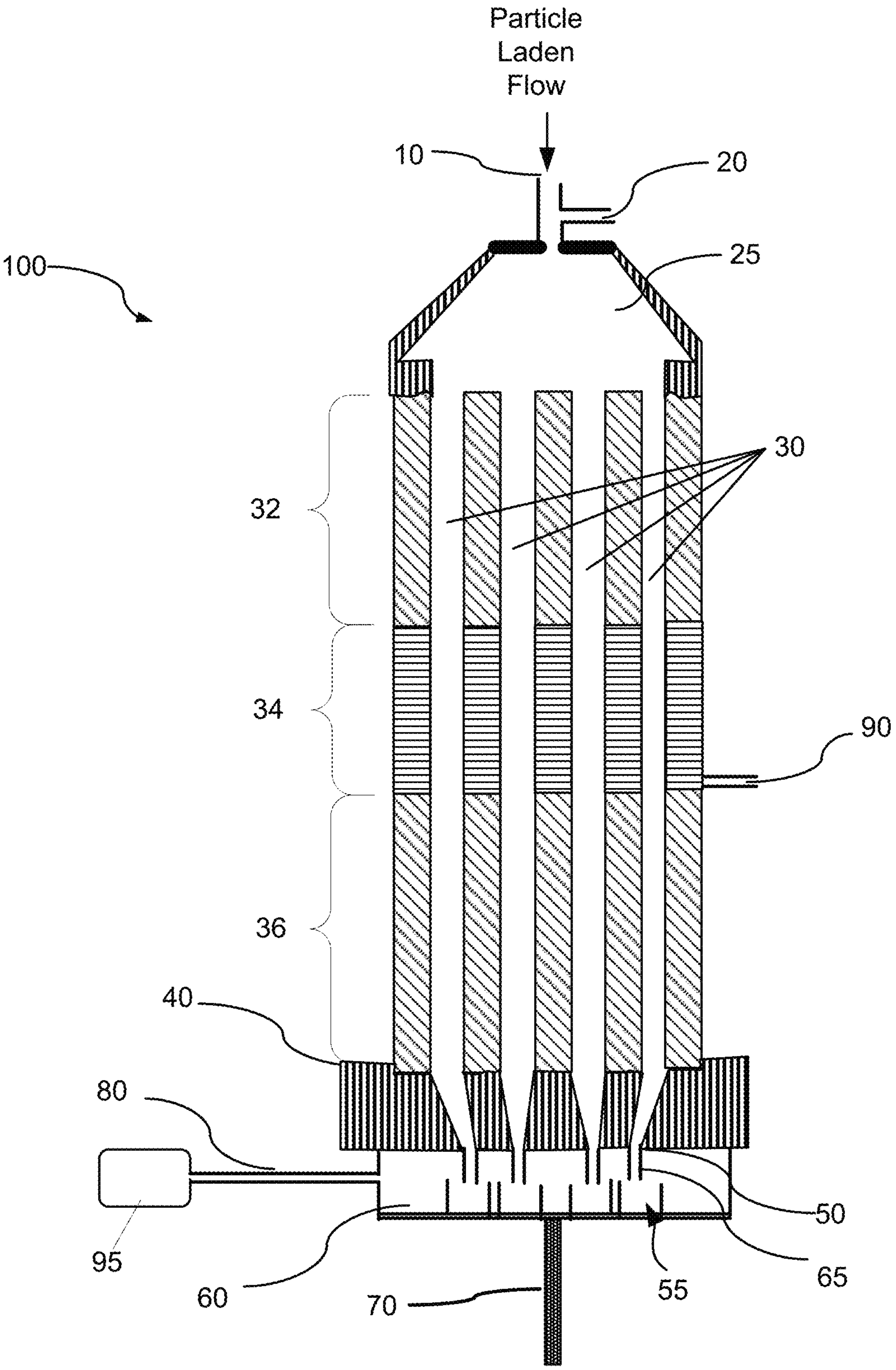
FIG. 1A is a schematic of the delivery unit showing four growth tubes of an eight-growth tube Condensationally Enhanced Cell Exposure System.

Technology for cell exposure to airborne particles is provided. One general aspect includes an apparatus. The apparatus includes a sample inlet coupled to a growth tube having interior walls that are wet, the growth tube configured to operate at a first temperature along a first length of the tube which is adjacent to the inlet and a second temperature along a second length positioned between the first length and a growth tube outlet. The apparatus also includes a nozzle plate having a plurality of nozzles, each of the plurality of nozzles having an input configured to receive the output of the growth tube and an output in an exposure chamber, the exposure chamber adapted to hold cell cultures at an air-liquid interface positioned underneath the plurality of nozzles. The apparatus also includes a temperature regulator adapted to control a temperature of the exposure chamber. The apparatus also includes a controller including instructions operable to cause the controller to maintain a relative humidity within the exposure chamber by controlling at least the second temperature of the growth tube and the temperature of the exposure chamber.

Implementations may include any of the foregoing features and may further include a plurality of growth tubes and where the nozzle plate includes the plurality of nozzles for each of the plurality of growth tubes. The apparatus may further include a second inlet coupled to a CO2 source and provided adjacent to the sample inlet such that a sample flow provided to the sample inlet is mixed with CO2 from the second inlet. The growth tube may include a third stage positioned between the second length and the output, the third stage configured to have a third temperature, the third temperature adapted to be higher or lower than the second temperature. The apparatus may further include a connecting adapter positioned between the growth tube and the nozzle plate, the adapter including at least one channel positioned between the output of the growth tube and the inputs of the nozzles, the channel being straight or angled relative to an axis passing through a center of the growth tube to mate with the input of the nozzles. Each of the plurality of nozzles has a nozzle diameter, the nozzle diameter and the plurality of nozzles defining an impaction velocity of particles over a cell substrate in the exposure chamber. The temperature regulator may be configured to maintain the exposure chamber at a temperature which maintains cell viability based on a region of the respiratory system from which the cell originates. The temperature regulator may be configured to maintain the exposure chamber at about 37° C. in order to maintain cell viability. The apparatus may further include an exposure plate in the exposure chamber configured to mount one or more cell substrates for simultaneous exposure. The exposure plate is rotatable and including a rotation motor.

One general aspect includes a method including providing a growth tube having interior walls that are wet positioned between in input and an output, a nozzle coupled to the output to provide the output of the growth tube to an exposure chamber. The method also includes introducing a cell culture into the exposure chamber. The method also includes introducing a particle laden flow into the growth tube through the input. The method also includes controlling a first temperature along a first length of the growth tube and a second temperature greater than the first temperature along a second length of the growth tube flow such that a vapor pressure of a condensing vapor at walls of the second length is near saturation to create enlarged particles in the particle laden flow. The method also includes simultaneously controlling a temperature of the exposure chamber such that a relative humidity within the exposure chamber is maintained by a combination of the temperature of the second length of the growth tube and the temperature of the exposure chamber.

Implementations may include any of the foregoing features including adding CO2 into particle laden flow in an amount sufficient to maintain a PH of the cell culture. The method may further include providing the growth tube with a third stage positioned between the second length and the output, and controlling the third stage to have a third temperature, the third temperature adapted to be higher or lower than the second temperature. The method may further include providing a number of nozzles and nozzle diameter selected to control an impaction velocity over the cell culture. The controlling the temperature of the exposure chamber at a temperature maintains cell viability based on a region of the respiratory system from which the cell originates. in order to maintain cell viability. The method may further include an exposure plate in the exposure chamber, and the method includes modifying the exposure plate to hold one or more cell inserts for simultaneous exposure of multiple cell cultures, each of which may be from single cell line, or from multiple cell lines. The modifying includes printing 3d cell inserts and culture dishes. The method includes maintaining the cell culture steady in the exposure chamber thereby providing localized deposition of enlarged particles in the flow. The method includes rotating the cell culture in the exposure chamber.

One general aspect includes an apparatus. The apparatus also includes a sample inlet coupled to a plurality of growth tubes, each growth tube having interior walls that are wet and configured to operate at a first temperature along a first length of the tube which is adjacent to the inlet and a second temperature along a second length positioned between the first length and a growth tube outlet. The apparatus also includes a nozzle plate having a plurality of nozzles associated with each growth tube, each of the plurality of nozzles having an input configured to receive the output of one of the plurality of growth tubes and an output in an exposure chamber, the exposure chamber adapted to hold cell cultures at an air-liquid interface in a position below the plurality of nozzles. The apparatus also includes a temperature regulator adapted to control a temperature of the exposure chamber. The apparatus also includes a controller including instructions operable to cause the controller to maintain a relative humidity within the exposure chamber by controlling at least the second temperature of the growth tube and the temperature of the exposure chamber. This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

DETAILED DESCRIPTION

The technology pertains to the delivery and deposition of particles suspended in air or other gas onto air-liquid-interface (ALI) cell cultures. More specifically, the technology pertains to devices and methods in which the size of particles is enlarged through condensation of water vapor onto the particle prior to delivery, and subsequently gently depositing the enlarged particles by inertial means. The present technology, referred to as a Condensationally Enhanced Cell Exposure System (CECES), overcomes limitations of prior technologies by providing efficient, gentle and controlled dose deposition of airborne particles as small as a few nanometers in diameter onto cells at the air-liquid interface. By enlarging particles using water-based condensational growth, small airborne particles as small as 5 nm can be gently deposited onto the surface of the cells without damaging the cellular membrane.

Commercially available instruments used for the delivery of airborne particles to ALI cell cultures are mainly based on four principles: diffusion/sedimentation, electrostatic deposition, droplet deposition and thermophoresis. All these techniques have very low deposition efficiency, have shown considerable differences in particle deposition among the exposed cell cultures, and yield dose calculations which are not accurate.

The CECES of the present technology uses condensational growth and particle impaction technologies to provide efficient delivery of airborne particles, independent of particle size and composition, onto the ALI in vitro model, and allow correct determination of the deposited particle dose for accurate dose dependent toxicity.

CECES utilizes the laminar-flow water-based condensational growth technology (such as that taught in U.S. Pat. No. 6,712,881 or U.S. Pat. No. 8,801,838) to condensationally enlarge particles as small as a few nanometers in diameter. These laminar flow techniques create a region of water vapor supersaturation within a laminar flow by passing the air sample through a wet-walled tube, the first portion of which has walls that are at a lower temperature than the subsequent, second section. The second stage can optionally be followed by a third stage, typically with cooler wall temperatures than the second stage. The third stage is used to control the water vapor content of the flow as it exits the tube. Although most commonly this condensation approach consists of one or more cylindrical tubes, it can also be done using parallel plate geometry. For either geometry, the term "growth tube" refers to a wet-walled container with two or more temperature regions through which the flow passes to create the condensational growth onto the particles suspended within the flow. Typically, this condensational enlargement increases the size of the particles to more the 1 micrometer in diameter. These enlarged particles are then gently deposited onto the cell culture surface by inertial means. CECES provides efficient deposition of airborne particles, independent of particle size and composition, onto the ALI in vitro model, allowing correct determination of the deposited particle dose for accurate dose dependent toxicity.

Figure 1B:
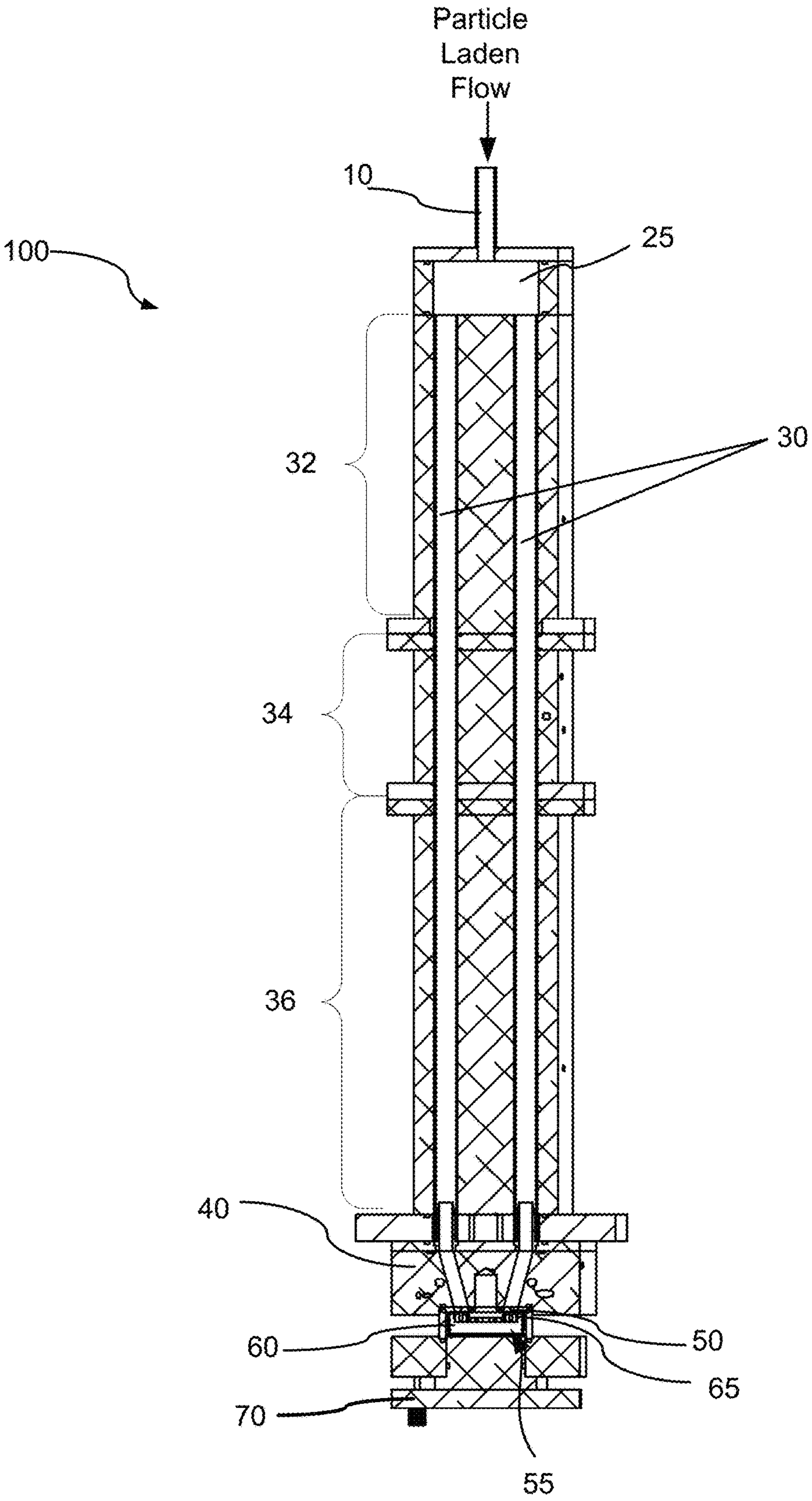
FIG. 1B is a mechanical cross section of Condensationally Enhanced Cell Exposure System.

A first embodiment of a CECES is illustrated in FIGS. 1A and 1B. FIG. 1A is a schematic diagram illustrating the major components of the CECES. FIG. 1B is a mechanical cross section of the CECES unit. A particle laden flow such as air containing the particles to be delivered is introduced through an inlet 10 and may be mixed with $CO_2$ flow coming from a side inlet 20. The flow and $CO_2$ sources are not illustrated in FIGS. 1A and 1B. The flow then enters an inlet chamber 25 and is split between multiple growth tubes 3 were particles are grown into micrometer size droplets by water condensation. As described herein, various numbers of growth tubes may be utilized in accordance with the technology. Each growth tube is provided with wet walls which may consist of a wick material wetted by injecting water into the material from an injection pump (not shown). Typically, the water injection is of a few microliters, and occurs a few times per minute. Excess water is removed at the bottom of the wick using a similarly sized ejection pump, or small flow (not shown). A short standpipe at the bottom of the wick ensures that excess water from the wick is not conveyed with the flow directed to the exposure chamber.

After condensational growth in each growth tube, a droplet laden flow exits each growth tube and is directed through an adapter plate 40 to a nozzle plate 50 and enters the exposure chamber 60, in which the cell culture is housed. The adapter plate contains channels connecting the exit of each growth tube to the inlet of one or more nozzles 65 housed on the nozzle plate 50. These channels may be slanted to allow the spacing among the nozzles to differ from that of the growth tubes. Most typically, these channels are slanted towards the center axis, thereby providing a more concentrated deposition to the substrate at the bottom surface 55 of the exposure chamber 60. The droplet laden flow is accelerated in the nozzles, impinges onto the cell culture on surface 55, and exits the chamber 60 through port 80. The droplet laden flow my be pulled by pump 95 from the chamber 60. Due to their inertia, the droplets cannot follow the (curved) flow exiting port 80, and instead tend to follow a straighter trajectory and deposit on the cell culture. The parameters for ensuring deposition of the droplets are governed by a dimensionless number, the Stokes number, as described below. The cell culture (and surface 55) may be housed on a stationary or rotating platform 70. Multiple cultures may be positioned, one under each nozzle 65. The rotating platform 70 may rotate all such cultures in the exposure chamber 60 together, or may include an assembly (described below) to rotate each cell culture sample individually relative to a respective nozzle under which the culture is positioned. Although illustrated with multiple tubes, the number of growth tubes 30 can vary from a single tube to multiple tubes, configured in varying patterns. For an eight-tube configuration, the growth tubes 30 are arranged in a circle, evenly spaced such that with center axis are each offset by 45° angle.

The sampling flow (i.e. the flow rate in the growth tubes) is typically in the range of 0.2 to 1.5 L/min per tube, with higher flows requiring longer growth tubes 30. The length of the tube 30 will determine the maximum sampling flow rate of CECES. The relationship between the sampling flow rate and the length of the growth tube has been established in U.S. Pat. Nos. 6,712,881 and 8,801,838). Typically, the flow rate is of the order of 0.5-1.5 L/min per tube, and the length of each tube is 280 mm with a diameter of 9.5 mm.

The growth tubes 30 may be configured with either two or three temperature stages. The conditioner 32, or first stage, is maintained cold. Its walls are held at a nearly constant temperature that is typically set at a value between 2 and 10° C. Typically, the conditioner 32 comprises 30% to 50% of the length of the growth tube. The second stage, referred to as the initiator 34, has warm walls, and are maintained at a fixed value that is at least 25° C. above the temperature of the conditioner 32, and typically it is set in the range between 27 and 60° C. The diffusion of water vapor from these warm walls into the cooler flow entering from the conditioner creates the supersaturated environment which initiates the condensational growth. Typically, the length of the initiator 34 is around 20%-30% of the total growth tube length. The third stage is referred to as the moderator 36, and comprises the remaining length of the growth tube. It may be operated with either cold or warm walls, depending the desired temperature for the exposure chamber 60, which in turn depends on the biological requirements of the target cells. Its function is to control the water vapor content of the sampling flow prior to exiting the growth tube and entering the nozzles and finally, the exposure chamber. The colder the walls of the moderator 36, the less vapor content in the exiting flow at the nozzles and the colder the exposure chamber 60 can be without introducing unwanted vapor condensation. In a two-stage system the initiator 34 and moderator 36 have the same wall temperature.

The walls of each growth tube 30 are lined with a wick material that is saturated with water. Several types of material have been used for this wick. One option is a porous plastic material that is treated to be hydrophilic. Another option is a rolled membrane filter material, such as Durapore® (Merk Industries). In both instances water is injected into the wick to maintain the water saturation. It has been shown that the rolled membrane filter is more effective, and for the same operating conditions yields larger droplets.

The sampling flow containing the condensationally enlarged particles reaches the nozzle plate through an adapter 40. This adapter 40 connects the bottom exit of the growth tubes with the nozzle plate 50. The adapter 40 may be heated to match the nozzle plate temperature. The flow lines in the adapter can be straight or slanted connections to fit the nozzle pattern, as noted above. Together with the nozzle plate 50, the adapter 40 will provide flexibility for increasing or decreasing the exposure chamber size in order to expose a different number of cell cultures. It should be recognized that the adapter and nozzle plate may be integrally formed as a single piece, or the adapter plate removed, in other embodiments of this technology.

Following the adapter 40, the enlarged particles enter the exposure chamber 60 after passing through a nozzle plate 50, designed to efficiently deliver the enlarged particles. This plate 50 is heated using a heating cartridge and a thermistor (not shown) to control the temperature. The temperature of the nozzles 65 is kept slightly higher than the moderator temperature to eliminate water condensation in the nozzle area. The number of nozzles and their nozzle diameter is optimized to achieved high deposition efficiency at low jet velocities output from the nozzles. Inertial impaction is governed by the Stokes number (Equation 1), which may be written in terms of the volumetric flow per nozzle Q where $D_{jet}$ is the nozzle diameter; $D_p$ is the particle diameter; $\rho_p$ is the particle density; $\mu_{air}$ is the viscosity of air; and C is the Cunningham slip factor:

$$St = \frac{4C_c\rho_p D_p^2 Q}{9\pi D_{jet}^3 \mu_{air}} \qquad \text{(Eq.1)}$$

Alternatively, it may be expressed in terms of the mean velocity of the air exiting each nozzle, V:

$$St = \frac{C_c \rho_p D_p^2 V}{9\pi D_{jet}^3 \mu_{air}} \quad \text{(Eq.2)}$$

For the geometry of the CECES, those droplets which upon acceleration through the nozzle obtain a St>0.2, will deposit on the ALI surface. The larger the particle, the lower the jet velocity output from each nozzle that is required for efficient deposition. The growth tube of the CECES system typically produces droplets with diameters in the range of 2 μm to 3 μm, or larger. The particle growth and final particle droplet size depends on the particle number concentration on the sampling air. However, this effect can be minimized by narrowing the growth tube diameter.

The size of the droplets that exit the growth tube may be above 2 μm or may be above 3 μm, depending on the exact configuration of the growth tube, the wick material, and the operating parameters. Correspondingly, the nozzle diameters and flows are selected to yield a Stokes number above 0.2, in accordance with equation (1), thereby facilitating the efficient capture of the droplets of the size that exit the growth tube.

The CECES aims for efficient, yet gentle deposition of droplets exiting the growth tube onto the ALI culture. The number of nozzles, and the diameter of those nozzles, are selected to efficiently capture droplets of the size exiting the growth tube, at low velocities. According to the Stokes number, for the same droplet size, the jet velocity is reduced by using more, smaller nozzles per growth tube. If the growth tube is configured to give larger droplets, then more, larger nozzle diameters can be used to give sufficiently high value for the Stokes number to capture the droplets while maintaining low jet velocities.

Figure 2C:
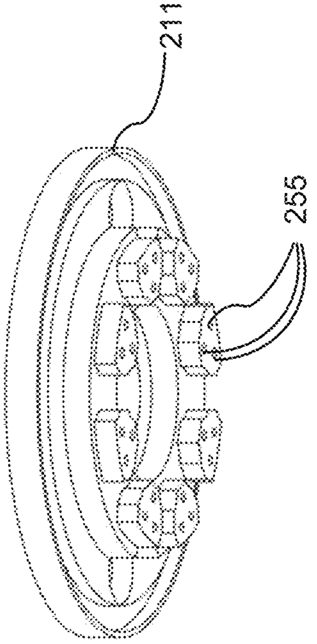
FIG. 2C is a perspective view and FIG. 2D a plan view showing a nozzle configuration for a system with 8 parallel growth tubes and 3 nozzles per growth tube.
Figure 2A:
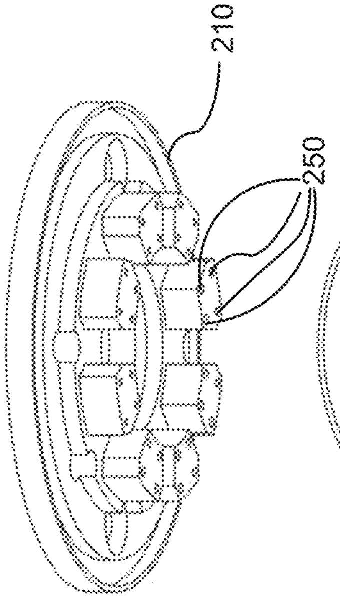
FIG. 2A is a perspective view, and FIG. 2B a plan view showing a nozzle configuration for a system with 8 parallel growth tubes and 4 nozzles per growth tube.
Figure 2D:
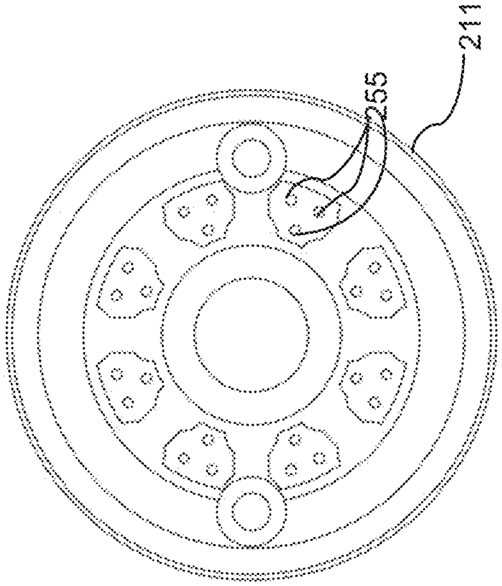
FIG. 2E shows the deposition pattern on the cell surface resulting from rotation of the collection surface.
Figure 2B:
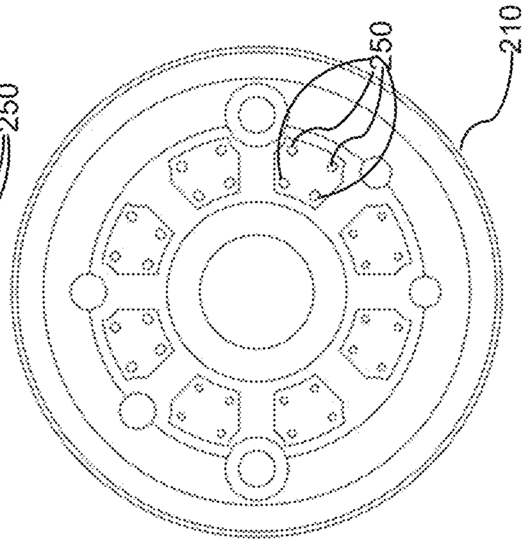
Figure 2E:
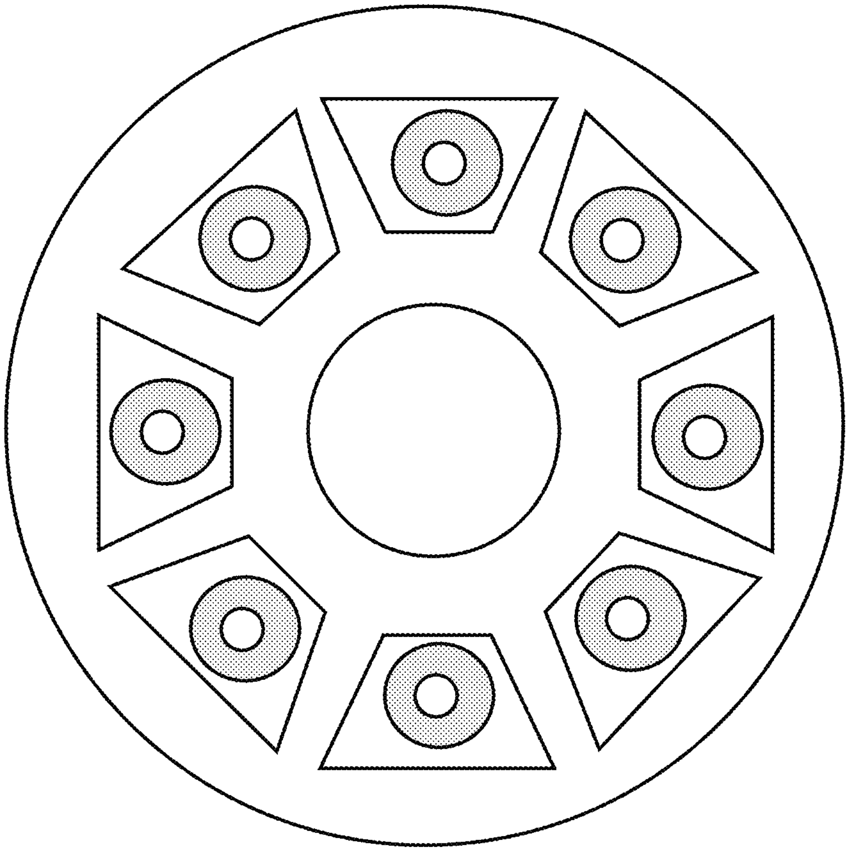

FIGS. 2A and 2*b* show an example of a nozzle plate 210 used in a CECES configured with eight growth tubes. The flow from each growth tube is delivered to a group of nozzles 250 on the nozzle plate 210. Each group of nozzles is comprised of four separate nozzles. FIGS. 2C and 2D show an alternate configuration for the nozzle plate of the eight-growth tube CESES. In FIGS. 2C and 2D the nozzle plate 211 has three separate nozzles 255 for each growth tube. For either configuration, each individual nozzle delivers a sample directly onto the surface of the cell culture, and the focused deposition achieved by impaction will form a similar pattern on the deposition surface. The deposition pattern for nozzle plate 210 for the four nozzle per growth tube configuration of FIG. 2A will match that of the nozzles when the deposition plate is stationary. Similarly, the deposition pattern for the three-nozzle configuration of FIG. 2C for a stationary deposition surface will match the three-nozzle pattern. The diameter of the deposition spot obtained is somewhat larger than the nozzle diameter, and for these two nozzle diameters is equal to 1 mm and 1.63 mm, respectively. As noted in FIGS. 1A and 1B, the deposition surface may be rotated to provide a uniform deposition pattern. FIG. 2E shows a uniform deposition pattern, which may be obtained by rotating a deposition surface under each individual set of nozzles.

The four-nozzle/jet configuration of FIG. 2A/2B was implemented using nozzles with a diameter of 0.66 mm. When sampling flow rate of 0.5 L/min/tube, the jet velocity is 6.1 m/s, and it will efficiently deliver and deposit droplets with a diameter larger than 1.8 μm, where the 1.8 μm diameter corresponds to a Stokes number St=0.22. The three-nozzle/jet configuration of FIG. 2C/2D was implemented with 1.0 mm nozzle diameters. At the same sampling flow rate, the jet velocity is 3.6 m/s, and particles with a larger than 3 μm diameter will have a St>0.22 and will be deposited efficiently.

CECES delivers particles by impaction onto cell cultures at the ALI. However, cell viability and stress resulting from the sampling protocol and method are of concern when using in vitro models for assessing toxicological outcomes associated with exposure to airborne particles. The impaction velocity of flow and particles onto the cell membrane at the air-liquid-interface, has a considerable effect on viability. Impaction velocities vary with the number and nozzle diameter of the nozzles delivering the sampling flow. Changes in the number of nozzles and nozzle diameter will change the Stokes number, and shifts the size of the smallest particle that can be collected. For the CECES configured as an eight-growth tube system employing the porous plastic wick, the droplet diameters were 2 μm and larger. To capture these 2 μm droplets, the nozzle plate was configured as in FIG. 2A, with four, 0.66 mm diameter nozzles per tube, and operated at 0.5 L/min per tube. This gives a velocity of the air impinging onto the ALI cell culture of 6.1 m/s. By changing to the more efficient, rolled membrane wick material, the size of the droplets exiting the growth tube increased to above 3 μm. These larger droplets are captured efficiently at lower jet velocities. Capture of these 3 μm droplets at the same sample rate of 0.5 L/min/tube is accomplished using the nozzle plate of FIG. 2B, with three, 1-mm diameter nozzles per tube. This configuration reduces the velocity of the impinging air flow, or impaction velocity, to 3.6 m/s.

Figure 3:
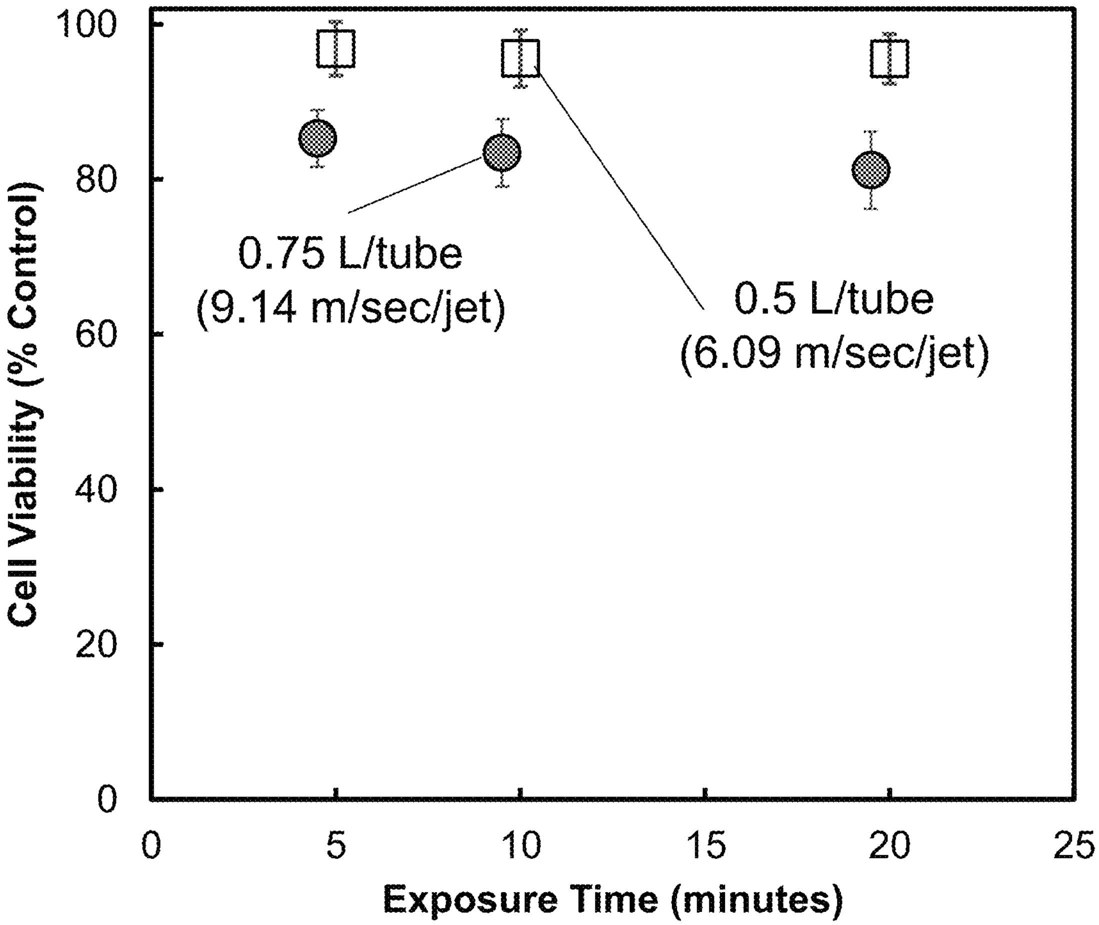
FIG. 3 is a graph of the cell viability with flow and exposure time in the unit.

FIG. 3 illustrates the effect of impaction velocities resulting from two different sampling flow rates of 4 and 6 L/min have in cell viability when exposing cells using an eight-tube system and four-nozzle plate (0.66 mm nozzle diameter) configuration of FIG. 2A. Testing was done over a range of exposure times. Control cells are kept in the exposure chamber sampling filter air for the same period of time as the cells exposed during the experiments, and cell viability measured as a percentage of the control. At 4 L/min and an impaction velocity of 6.1 m/s the effect on cell viability is minimum, with cell viabilities close to 100% of that for the control. For the 6 L/min sampling flow rate and impaction velocities of 9.1 m/sec, cell viability was reduced to around 85% with respect to the control. Impaction velocities lower than 22 m/s are needed to maintain acceptable cell viability. The ability to control and modify several parameters, including sampling flow, number of nozzles and nozzle diameter, to achieve high deposition efficiency while minimizing cellular damage is only feasible with CECES.

Figure 4A:
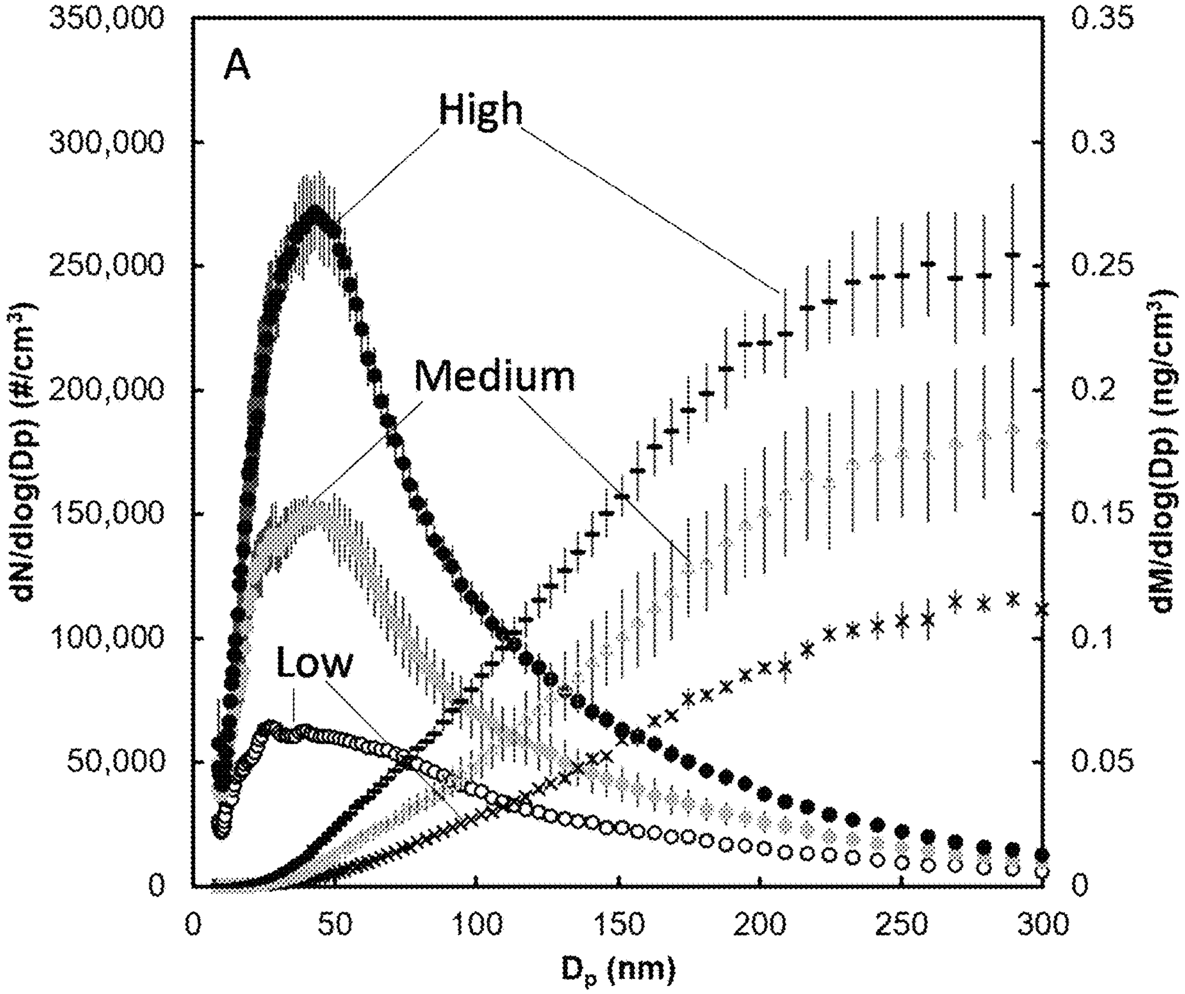
FIG. 4A is a graph showing particle size distribution of an aerosol used for testing.
Figure 4B:
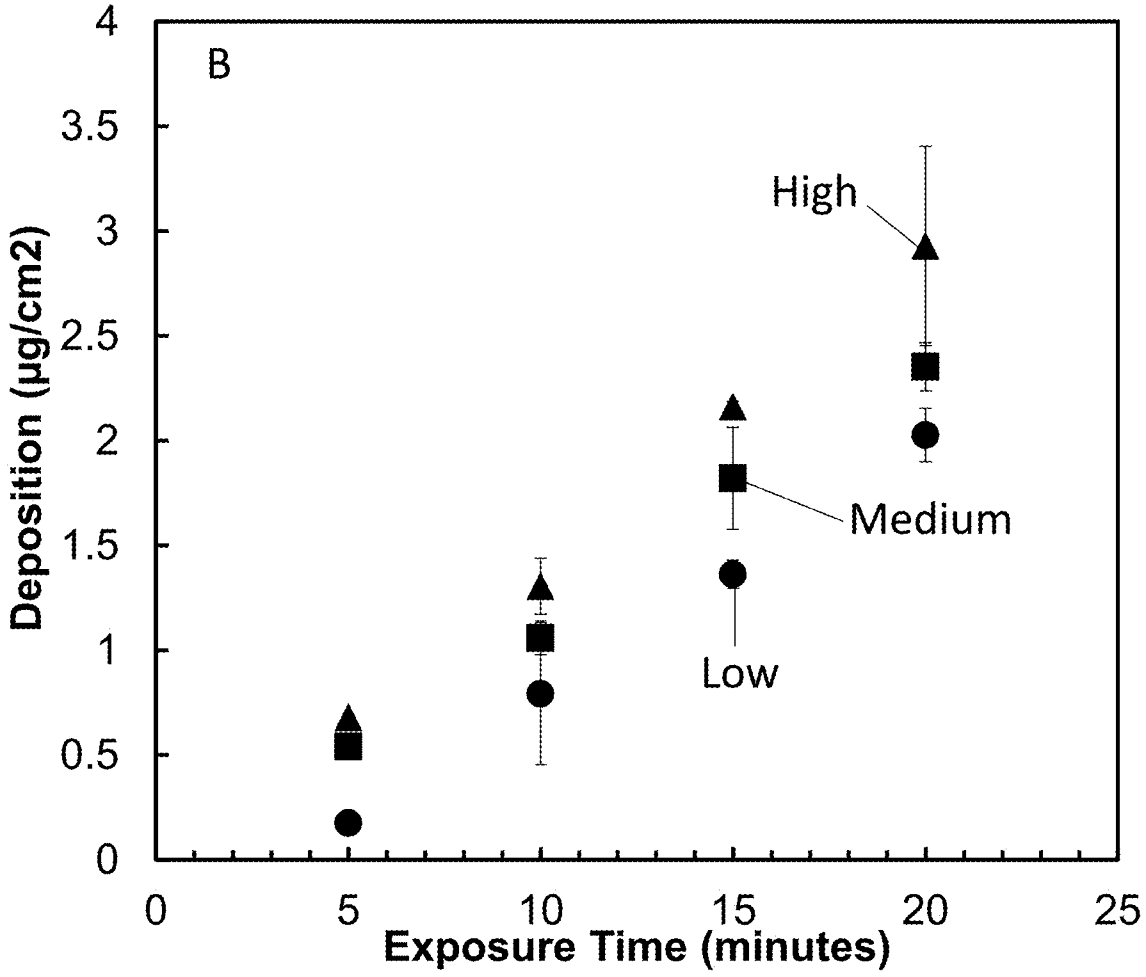
FIG. 4B is a graph of the delivery mass dose delivered to the exposed cells by the unit as a function of sampling flow rate and time for the aerosol of FIG. 4A.

CECES, using the water-condensational growth and inertial deposition, produces a considerably higher particle deposition per unit of time that any other exposure units. The deposited dose can be controlled by changing the particle number concentration in the sample air, modifying the sampling flow rate of CECES, and varying the exposure periods. FIGS. 4A and 4B illustrate differences in the deposition dose achieved by this method with variations in these parameters. FIG. 4A describes the particle number concentration and mass distribution of generated aerosol in the sampling flow, at low, medium, and high concentrations. FIG. 4B depicts deposited dose for each of these three aerosol generation conditions for sampling with the at a CECES sampling flow rate of 4 L/min for various exposure times. Because of its concentrated, high deposition efficiency, CECES can provide deposited mass doses in the range of several $\mu g/cm^2$ within a period of minutes. This is much less time than required for existing methods.

To test the toxicity from exposure, the environmental conditions in the chamber housing the cell cultures must be controlled to be that required to maintain cellular viability and health. Typically, the temperature in the exposure chamber is kept at about 37° C., plus or minus 2° C. High relative humidity is controlled by the water vapor content of the incoming sampling flow after which, in turn, is controlled by regulating the temperature of the third stage of the growth tube (moderator). The temperature of the moderator will dictate the water content of the exiting flow into the exposure chamber. Relative humidity is kept at values higher than 90% for ideal exposure conditions.

For long exposure times, the culture media feeding the ALI cells, requires that its pH be constant during exposure. When sampling an air stream at ambient $CO_2$ levels, the cell culture medium is disturbed by the sampling flow which over times produces changes in the pH. To maintain the properties of the culture medium, CECES provides a side flow inlet 20 to add $CO_2$ to the sampling flow so that the air entering the exposure chamber 60 contains 5% $CO_2$. The CO2 level is controlled by adjusting the CO2 side flow introduced at port 20.

With CECES it is possible to expose multiple cell cultures simultaneously. The exposure chamber can support up to 1 cell culture insert per growth tube; the number of growth tubes will define the maximum number of ALI cell culture that can be exposed at any given time. Multiple cell cultures can be exposed simultaneously.—a single cell line can be exposed for comparison and statistical power, or multiple cell lines can be exposed simultaneously. For example, the multiple cell lines may include human bronchial epithelial cells (BEAS-2B), Normal Human Bronchial/Tracheal Epithelial cell line (NHBE), or human macrophage cell lines (RAW 264.7).

The cell inserts and the cell culture dish plate holder are manufactured using 3D printing, for fast and cheap production. 3D printing technology offers the means to design and modify cell insets into shapes and configurations for easy adaptation into the exposure chamber of CECES. Square or round culture inserts that fit into the cell dish plate can be used for exposure when using a stationary platform, while round-geared inserts are needed when rotation is required for homogeneous particle deposition. Configurations can be quickly modified and printed. Cell culture inserts fit into the culture plate holder which is then inserted into place in the exposure chamber. The plate holder can be also modified for holding 1 (35 mm dish) to 16 cell inserts (6 mm insert), and to support the drive gear for rotation. The plate holder and cell culture dishes are designed for user friendly interface.

Figure 5A:
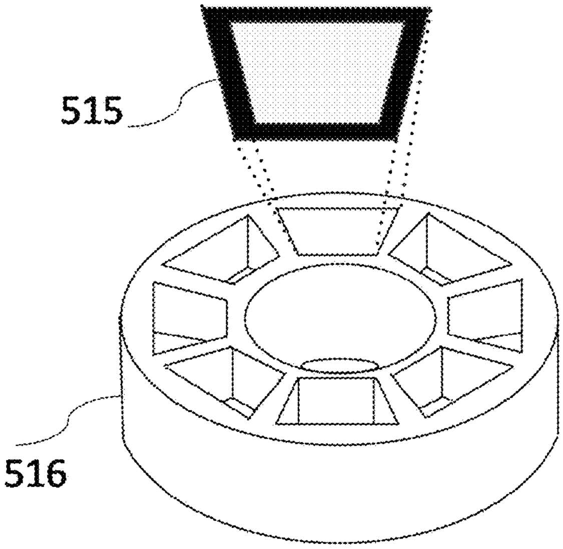
FIG. 5A illustrates a first cell insert and configuration of the plate holder manufactured using 3D printing.
Figure 5B:
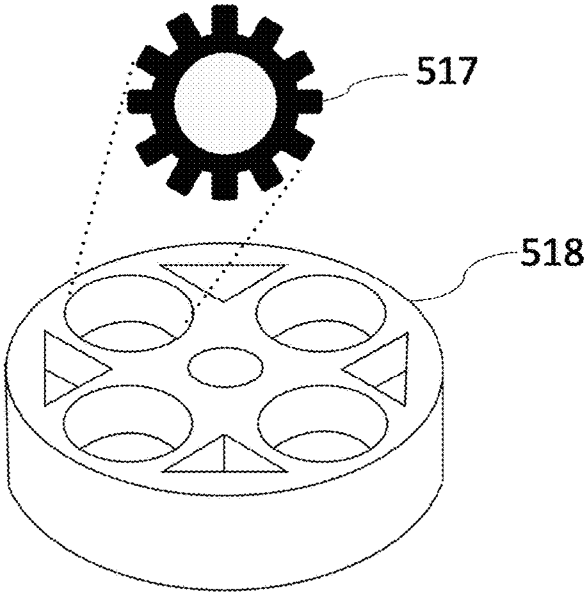
FIG. 5B illustrates a second cell insert and configuration of a plate holder manufactured using 3D printing.

FIG. 5A presents examples of 3D printed shapes and configurations for a square insert 515 that fits into an eight-culture plate holder 516. FIG. 5B illustrates round, geared inserts 517 that fit into a four inserts plate holder 518. The round, geared inserts 517 allow each cell culture positioned in an insert to be individually rotated relative to the nozzles to produce the deposition pattern shown in FIG. 2E. The material of the cell inserts is selected for compatibility with the cell line exposed using CECES. Similarly, the material of the plate holder will be compatible with decontamination or autoclaving processes. Disposable materials can be used for eliminating contamination from one experiment to another.

With CESES, the deposition pattern can be configured to be to what happens in the lung. By using a stationary platform for the cell culture (FIG. 5A), the CESES provides localized deposition mimicking deposition on lung bifurcation points. By rotating the platform holding the cell culture (FIG. 5B), the deposition pattern (FIG. 2E) is more homogeneous, mirroring deposition of smaller particles in lower lung regions.

Impaction delivers highest concentration of particles directly below the nozzle. The time at which a single spot on the cell culture surface is exposed to the delivery flow can be reduced by rotating the exposure culture insert. Rotating the insert will also provide a homogeneous deposition of the incoming particles over the complete surface of the culture. Regional lung deposition of particles is driven by the mechanisms governing particle movements; for larger particles inertial impaction on localized areas (mainly bifurcations) is the main mechanism, while smaller particles can reach deeper areas and by diffusion deposit more evenly on the lung surfaces.

Figure 6A:
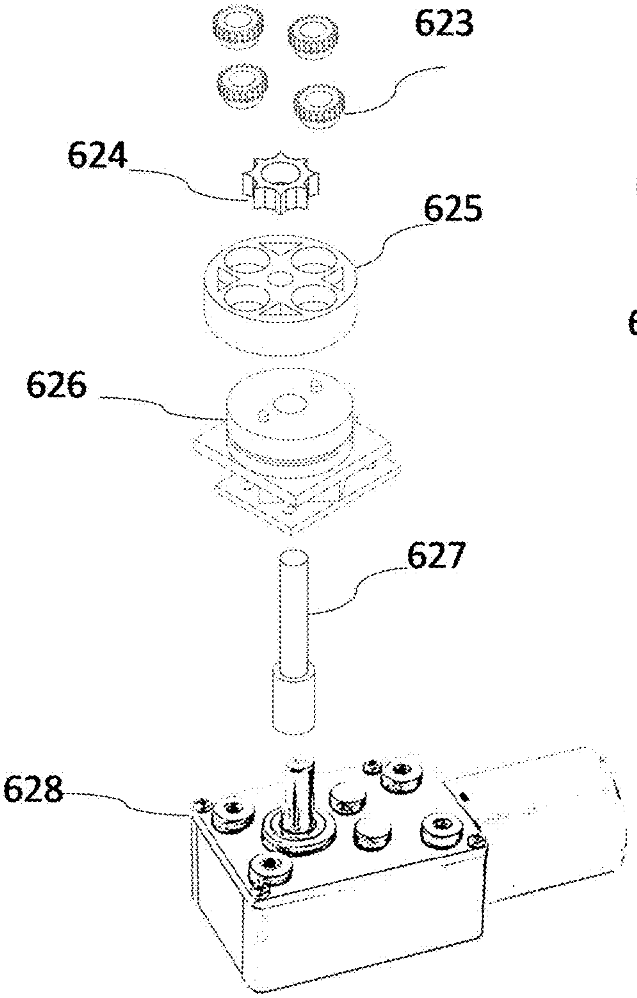
FIG. 6A is an assembled, perspective view, and FIG. 6*b* and exploded view, of a rotating platform of the cell deposition chamber. Like numbers represent like parts throughout the figures.
Figure 6B:
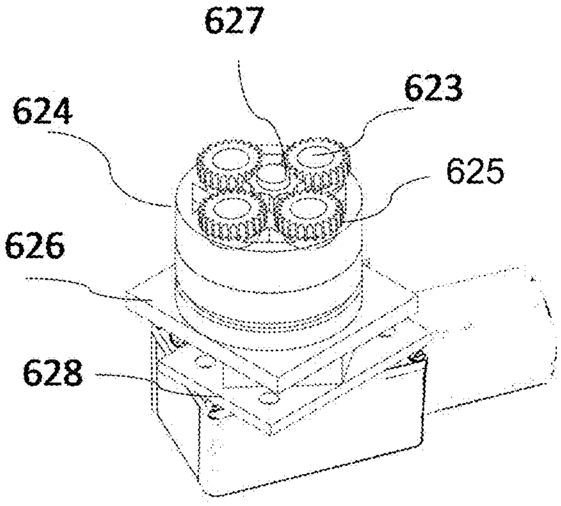

By rotating the cell culture dish, the exposure can be equalized across the entire cell culture surface as mimic the deposition of the smaller particles over a larger surface. The platform used for rotation of the individual cell culture dishes for homogeneous distribution is illustrated in FIGS. 6A and 6B. FIG. 6A is an exploded view, and FIG. 6B an assembled view, of the rotational platform 600. Geared cell culture inserts 623 are placed onto the cell culture dish 625 using the drive gear 624 to hold the inserts in place for rotation. The assembly fits into the motor adapter 626 which will later place the cell cultures into the unit's exposure chamber shown in FIG. 1A/1B. The drive shaft 627 will be inserted into the assembly and the worm drive motor 628 will rotate the cell cultures. The drive shaft is attached to a low speed worm gear motor box (such as 20 rotations per minute), which fits into the motor adaptor. The motor adaptor has a rubber gasket between it and the motor box to prevent loss of vacuum and change in flow rate during cell exposure in CECES. The motor adaptor has two pins that allow the cell culture exposure dish to snap in place and be oriented directly under the exposure nozzles. The drive gear snaps onto the drive shaft which goes through the center of the motor adaptor and cell culture exposure dish so that the drive gear is on top of the cell culture exposure dish. The drive gear has eight teeth and can rotate each cell culture six times an hour. The homogeneous deposition 214 obtained when the rotating platform is used is illustrated in FIG. 2E. The speed of the rotation is controlled by the worm drive motor. Changing this motor will result in faster or slower rotations, with lower or higher loading or dose deposited at an individual surface spot.

Figure 7:
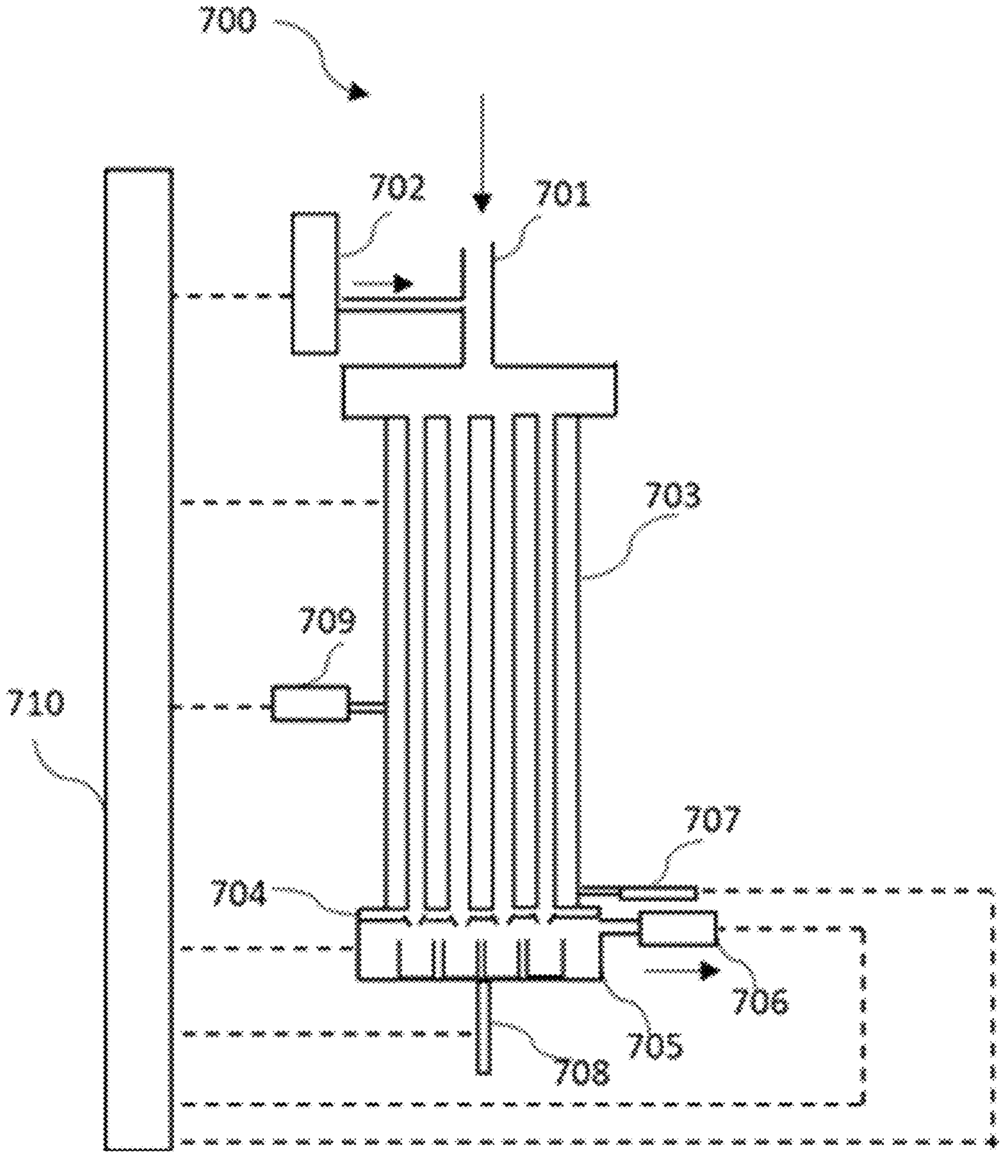
FIG. 7 is an example apparatus utilizing water-based condensational growth to expose cell cultured at the air-liquid-interface to airborne nanoparticles

FIG. 7 is an example apparatus utilizing water-based condensational growth to expose cell cultured at the air-liquid-interface to airborne nanoparticles. The apparatus 700 consists of a main inlet 701 for the air sample of particle-laden and a side inlet 702 for $CO_2$ addition, which introduces the sample into a condensational growth tube 703 for condensationally enlarging the particles from diameters as small as a few nanometers to micrometer sizes, a nozzle plate 704 for delivery and deposition of the enlarged particles, an exposure chamber 705 where the cells are exposed to the enlarged particles, an exhaust line and pump 706 where the flow exits the chamber, a motor 707 for rotational exposure, a water injection pump to deliver water to maintain the wicks wet, and a water removal pump 709 to remove extra water. All parameters required for optimum performance of the system, (1) $CO_2$ flow, (2) growth tube temperatures, (3) water injection and removal pumps, (4) exposure chamber environmental conditions, (5) sampling pump, and (6) rotational motor speed, are all regulated by the controller 710.

The controller may be configured to perform the methods described herein and may comprise any of a general-purpose network component or computer system which includes a processor (which may be referred to as a central processor unit or CPU) that is in communication with memory. The processor may comprise multiple processors implemented as one or more CPU chips, cores (e.g., a multi-core processor), FPGAs, ASICs, and/or DSPs, and/or may be part of one or more ASICs. The controller may be configured to implement any of the schemes described herein. The processor may be implemented using hardware, software, or both.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, it is noted that the term "based on" as used herein, unless stated otherwise, should be interpreted as meaning based at least in part on, meaning there can be one or more additional factors upon which a decision or the like is made. For example, if a decision is based on the results of a comparison, that decision can also be based on one or more other factors in addition to being based on results of the comparison.

Embodiments of the present technology have been described above with the aid of functional building blocks illustrating the performance of specified functions and relationships thereof. The boundaries of these functional building blocks have often been defined herein for the convenience of the description. Alternate boundaries can be defined so long as the specified functions and relationships thereof are appropriately performed. Any such alternate boundaries are thus within the scope and spirit of the claimed invention.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the embodiments of the present technology without departing from its scope. While the dimensions, types of materials and coatings described herein are intended to define the parameters of the embodiments of the present technology, they are by no means limiting and are exemplary embodiments. Many other embodiments will be apparent to those of skill in the art upon reviewing the above description. The scope of the embodiments of the present technology should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. § 112(f), unless and until such claim limitations expressly use the phrase "means for" followed by a statement of function void of further structure.

We claim:

1. An apparatus, comprising:

a sample inlet coupled to a plurality of laminar flow, condensational growth tubes, the plurality comprising a number of growth tubes, each of the plurality of growth tubes having interior walls that are wet such that a sample flow entering the inlet is split between the plurality of growth tubes, each condensational growth tube configured to operate at a first temperature along a first length of the tube which is adjacent to the inlet and a second temperature along a second length positioned between the first length and a growth tube outlet, the tube in the second length comprising a supersaturation region within the condensation growth tube;

a nozzle plate having a plurality of nozzles, the plurality of nozzles comprising a number of nozzles, each of the nozzles having an input configured to receive the output of one of the plurality of growth tubes and an output in an exposure chamber, the input having a greater area than the output such that the output focuses enlarged particles to hold in vitro cell culture systems positioned at a distance from the output, each nozzle having a nozzle diameter; and a temperature regulator adapted to control a temperature of the nozzle plate and exposure chamber; and a controller including instructions operable to cause the controller to maintain a relative humidity within the exposure chamber by controlling at least the second temperature of the growth tube and the temperature of the exposure chamber, and controlling a flow rate of CO2 introduced into the apparatus;

wherein the first length, the second length, the tube diameter, the number of the plurality of growth tubes, the number of nozzles, and the nozzle diameter of each of the plurality nozzles are configured to produce an output velocity of a flow at the output of less than 22 m/s for a sampling flow rate of 6.0 L/m and a deposition efficiency at inertial impaction velocities having a Stokes number above 0.2.

2. The apparatus of claim 1 wherein the nozzle plate includes one or more nozzles for each of the plurality of growth tubes, each nozzle having a converging flow guiding section between the input and the output exiting into the exposure chamber, the flow guiding section reducing a cross-sectional area of the incoming flow path.

3. The apparatus of claim 1 further including a second inlet coupled to a $CO_2$ source and provided adjacent to the sample inlet such that a sample flow provided to the sample inlet is mixed with $CO_2$ from the second inlet.

4. The apparatus of claim 1 wherein the condensational growth tube includes a third length positioned between the second length and the output, the third stage configured to have a third temperature, the third temperature adapted to be higher or lower than the second temperature and adapted to remove excess water vapor content in a supersaturated flow.

5. The apparatus of claim 4 further including a flow guiding adapter positioned between the third length of the growth tube and the nozzle plate, the flow guiding adapter including at least one channel positioned between the output of the condensational growth tube and the inputs of the nozzles, the channel being straight or angled relative to an axis passing through a center of the growth tube to mate with the input of the one or more nozzles.

6. The apparatus of claim 1 wherein the temperature regulator is configured to maintain the exposure chamber at a temperature which maintains cell viability based on a region of the respiratory system from which the cell originates.

7. The apparatus of claim 6 wherein the wherein the temperature regulator is configured to maintain the exposure chamber at about 37° C. lung cell viability or other temperatures for cells at other regions of the respiratory system.

8. The apparatus of claim 1 further including an exposure plate in the exposure chamber configured to mount one or more cell substrates for simultaneous exposure.

9. The apparatus of claim 8 wherein the exposure plate is rotatable and including a rotation motor.

10. An apparatus, comprising:

a sample inlet coupled to a plurality of growth tubes such that a sample flow provided to the inlet is split between the plurality of growth tubes, each growth tube having interior walls that are wet and configured to operate at a first temperature along a first length of the tube which is adjacent to the inlet and a second temperature along a second length positioned between the first length and a growth tube outlet;

a nozzle plate having a plurality of nozzles, at least one of the plurality of nozzles associated with each growth tube, each of the plurality of nozzles having an input configured to receive the output of one of the plurality of growth tubes and an output in an exposure chamber, the exposure chamber adapted to hold cell cultures at an air-liquid interface in a position below the plurality of nozzles, each nozzle having a nozzle diameter, and a temperature regulator adapted to control a temperature of the exposure chamber; and a controller including instructions operable to cause the controller to maintain a relative humidity within the exposure chamber by controlling at least the second temperature of the growth tube and the temperature of the exposure chamber, and controlling a flow rate of sampling flow introduced into the apparatus;

wherein the first length, the second length, the tube diameter and the nozzle diameter of each of the one or more nozzles are constructed to produce an output velocity of a flow at the output of less than 22 m/s for a sampling flow rate of 6.0 L/m.

11. An apparatus, comprising:

a sample inlet coupled to a plurality of growth tubes such that a sample flow provided to the inlet is split between the plurality of growth tubes, the plurality comprising a number of growth tubes, each of the growth tubes having interior walls that are wet, each growth tube configured to operate at a first temperature along a first length of the tube which is adjacent to the inlet and a second temperature along a second length positioned between the first length and a growth tube outlet;

a nozzle plate having a plurality of nozzles, the plurality of nozzles comprising a number of nozzles, each of the plurality of nozzles having an input configured to receive the output of one of the plurality of growth tubes and an output in an exposure chamber, the exposure chamber adapted to hold cell cultures at an air-liquid interface positioned underneath the plurality of nozzles, each of the plurality nozzles has a nozzle diameter;

a temperature regulator adapted to control a temperature of the exposure chamber; and a controller including instructions operable to cause the controller to maintain a relative humidity within the exposure chamber by controlling at least the second temperature of the growth tube and the temperature of the exposure chamber, and controlling a flow rate of sampling flow introduced into the apparatus;

wherein the first length, the second length, the tube diameter, the number of the plurality of growth tubes, the number of nozzles, and the nozzle diameter of each of the plurality of nozzles are constructed to produce an output velocity of a flow at the output of less than 22 m/s for a sampling flow rate of 6.0 L/m and a deposition efficiency at inertial impaction velocities having a Stokes number above 0.2; and wherein the exposure plate is rotatable and including a rotation motor.

* * * * *